(12) United States Patent  (10) Patent No.: US 8,397,715 B2
Litz  (45) Date of Patent: Mar. 19, 2013

(54) CHEMICAL AND BIOLOGICAL PROTECTION MASK

(76) Inventor: Jeffrey C. Litz, Glen Burnie, MD (US)

( * ) Notice: Subject to any disclaimer, the term of this patent is extended or adjusted under 35 U.S.C. 154(b) by 946 days.

(21) Appl. No.: 12/456,431

(22) Filed: Jun. 16, 2009

(65) Prior Publication Data

US 2010/0132715 A1   Jun. 3, 2010

Related U.S. Application Data

(63) Continuation-in-part of application No. 12/385,482, filed on Apr. 9, 2009, now abandoned.

(60) Provisional application No. 61/193,432, filed on Nov. 28, 2008.

(51) Int. Cl.
*A62B 18/00* (2006.01)

(52) U.S. Cl. .......... 128/201.25; 128/201.28; 128/201.29

(58) Field of Classification Search . 128/201.12–202.11
See application file for complete search history.

(56) References Cited

U.S. PATENT DOCUMENTS

| | | | | |
|---|---|---|---|---|
| 6,233,748 | B1 * | 5/2001 | Gieger et al. | 2/410 |
| 6,681,765 | B2 * | 1/2004 | Wen | 128/201.25 |
| 6,983,745 | B2 * | 1/2006 | Tang et al. | 128/201.25 |
| 7,409,952 | B2 * | 8/2008 | Chen | 128/204.18 |
| 2007/0163588 | A1 * | 7/2007 | Hebrank et al. | 128/204.18 |
| 2007/0272244 | A1 * | 11/2007 | Witmer | 128/205.25 |
| 2009/0205664 | A1 * | 8/2009 | Lyon | 128/205.12 |

* cited by examiner

*Primary Examiner* — Lynne Anderson
(74) *Attorney, Agent, or Firm* — Ober, Kaler, Grimes & Shriver; Royal W. Craig

(57) ABSTRACT

A chemical and biological protection mask that combines a filter cartridge with a miniaturized high-intensity shortwave UV disinfecting system in a compact easy-to-wear and fully portable form factor. The gas mask comprises a mask portion for covering at least the nose and mouth of a user, a one way exhalation valve mounted on the mask portion, a coupling to an inhalation opening into the mask portion, a filter canister, and a novel UV-illumination tube attachable between the inhalation valve coupling and filter canister. The UV-illumination tube further comprises an aluminum tube, a plastic insert positioned inside the aluminum tube, and a plurality of circuit boards seated within the insert. The circuit boards each have a plurality of UV LED lights axially mounted thereon to irradiate and disinfect air passing through the UV-illumination tube. The UV LED lights preferably emit light within a range of from 240 nm~280 nm wavelength, and are powered by a battery connected to a voltage regulator. A current chopping circuit is connected between said voltage regulator and said UV LED lights for providing pulsed current thereto. An optional solar cell is disclosed for powering the UV LED lights directly or for recharging the battery, and the solar cell may be mounted atop a visor attached to said mask.

21 Claims, 4 Drawing Sheets

CHEMICAL AND BIOLOGICAL PROTECTION MASK

CROSS-REFERENCE TO RELATED APPLICATION(S)

The present application is a continuation-in-part of U.S. application Ser. No. 12/385,482 filed 9 Apr. 2009 now abandoned, and derives priority from U.S. provisional application Ser. No. 61/193,432 filed Nov. 28, 2008.

BACKGROUND OF THE INVENTION

1. Field of the Invention

The present invention relates to protective breathing devices, and, more particularly, to a chemical and biological protection mask that combines a filter cartridge with a miniaturized high-intensity shortwave UV disinfecting system.

2. Description of the Background

There is a wide variety of prior art with regard to gas masks and breathing gas respirators. Most conventional gas mask/respirators utilize a half-mask or full face mask that covers the nose and mouth and in the latter case the entire upper face.

Gas masks as described above use a face piece made of an impermeable material, resistant to chemical agents and a harness which allows the mask to be put on the user's head so as to provide a tight seal between the edges of the face piece and the user's face. Once the mask is put on, the user can inhale air from the outside through an inflow opening arranged on the face piece and provided with a threaded or twist-lock fitting. A filtering cartridge is inserted onto the fitting to decontaminate the air being inhaled. The air subsequently exhaled by the user is expelled from the mask through an outflow opening, also arranged on the face piece and provided with a one-way valve. The face piece comprises two eye-pieces or, alternatively, a single transparent screen to give the user full visibility.

Conventional gas mask/respirators invariably utilize a cartridge containing various filter media. In their simplest form, the cartridges incorporate a filter cloth, charcoal, or polymeric material that merely filters out particulate materials including sprays and colloidal suspensions. Those filters that rely on activated charcoal eliminate particulate material and also adsorb vapor and gas contaminants as they come in contact with the charcoal. The most effective filtration media is a HEPA-type filter formed of pleated filter paper with minute interstices for allowing the passage of air there through.

Despite their effectiveness against particulate materials and suspensions, the foregoing and other known filter-type gas masks are not sufficiently effective in filtering biological organisms such as viruses and germs. With the increased threat of biological warfare, there is currently a significant need for a gas mask/respirator capable of killing germs as well as filtering toxins.

In other application, chemical agents are often used to destroy or kill germs and bacteria. However, it particularly difficult to incorporate chemical mechanisms into a gas mask.

UV radiation is another known germicide. Germicidal ultraviolet (UVC) light kills cells by damaging their DNA. Ultraviolet photons harm the DNA molecules of living organisms, and the distorted DNA molecules do not function properly, cannot replicate, and eventually the cells die. High-intensity shortwave ultraviolet light is commonly used for disinfecting smooth surfaces such as dental tools, and ultraviolet light fixtures are often present in labs. Unfortunately, existing UV-light sources for biocidal applications are typically fluorescent UV light bulbs. These bulbs are large and require the presence of a ballast and AC power source for stable operation. The size requirements of high-intensity shortwave ultraviolet disinfectant systems are unsuitable for portable use in any gas mask, and so these systems are not known in this context.

There would be great advantage in a breathing gas mask or respirator that combines a filter cartridge with a miniaturized high-intensity shortwave UV disinfecting system, in a compact easy-to-wear and fully portable form factor.

SUMMARY OF THE INVENTION

It is, therefore, an object of the present invention to provide a combination chemical and biological protection mask.

It is another object to provide a combination chemical and biological protection mask in a compact portable self-contained form factor.

It is another object to provide a solar-powered combination chemical and biological protection mask.

It is another object of the present invention to provide a combination chemical and biological protection mask with a miniaturized low-power UV LED-light array These and other objects are achieved herein by a gas mask or respirator that combines a filter cartridge with a miniaturized high-intensity shortwave UV disinfecting system in a compact easy-to-wear and fully portable form factor. The gas mask comprises a mask portion for covering at least the nose and mouth of a user, a one way exhalation valve mounted on the mask portion, a coupling to an inhalation opening into the mask portion, a filter canister, and a novel UV-illumination tube attachable between the inhalation valve coupling and filter canister. The UV illumination tube further comprises an aluminum tube, a plastic insert positioned inside the aluminum tube, and a plurality of circuit boards seated within the insert. The circuit boards each having a plurality of UV LED lights axially mounted thereon to irradiate and disinfect air passing through the UV-illumination tube. The UV LED lights preferably emit light within a range of from 240 nm~280 nm wavelength, and are powered by a battery connected to a voltage regulator. A current chopping circuit is connected between said voltage regulator and said UV LED lights for providing pulsed current thereto. An optional solar cell is disclosed for powering the UV LED lights directly or by recharging the battery, and the solar cell may be mounted atop a visor attached to said mask.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

The present invention is a chemical and biological protection mask that combines a filter cartridge with a miniaturized high-intensity shortwave UV disinfecting system in a compact easy-to-wear and fully portable form factor.

Figure 1:
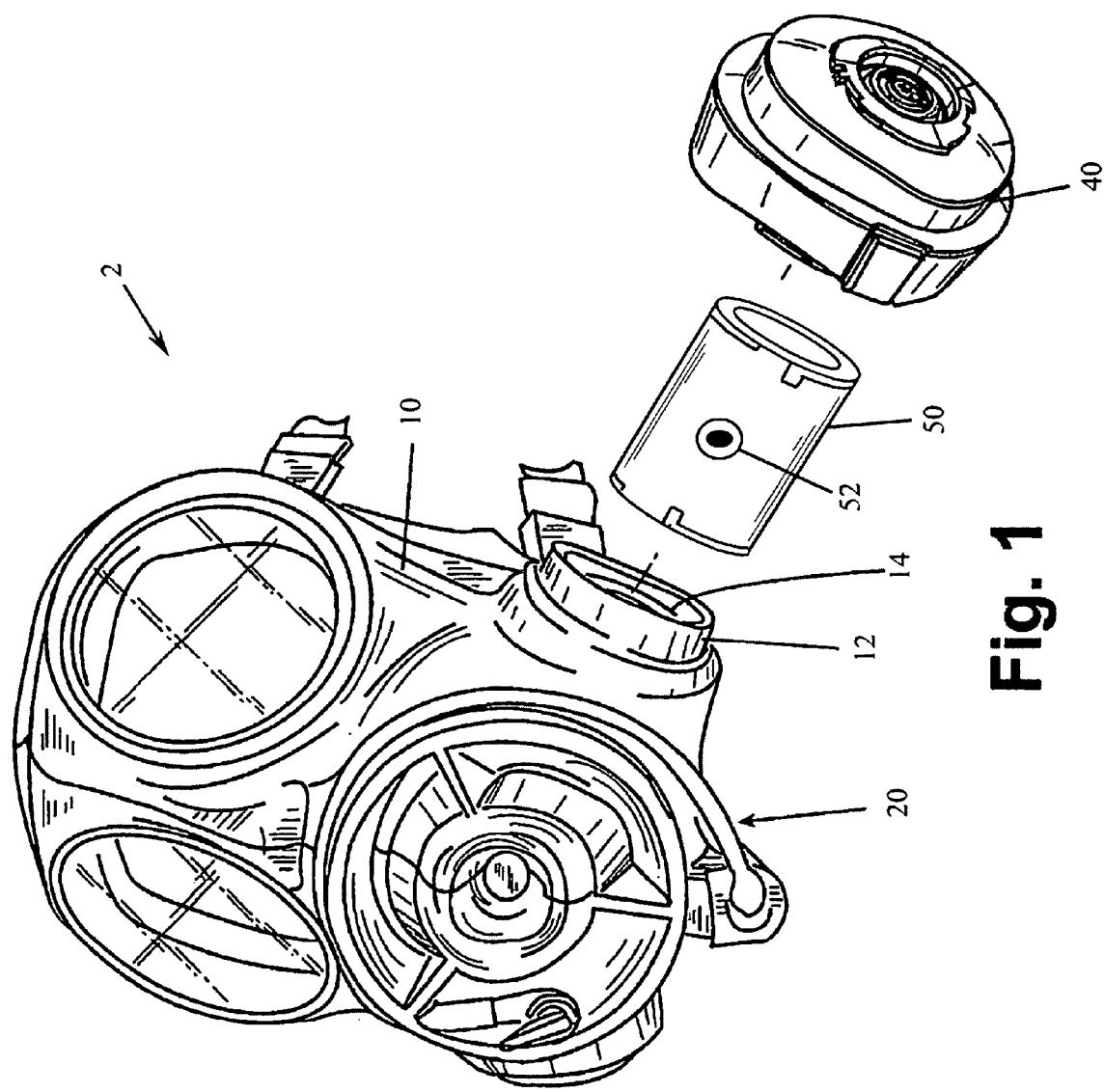
FIG. 1 is a front perspective view of the gas mask 2 according to an embodiment of the present invention.

FIG. 1 is a front perspective view of the gas mask assembly 2 according to an embodiment of the present invention. The gas mask assembly 2 generally comprises a molded mask portion 10 containing a frontal one-way exhalation valve 20 and one or more adjacent inhalation apertures 12. In the illustrated embodiment, the inhalation aperture 12 is equipped with a push-and-twist receptacle 14. In the prior art, a filter assembly 40 with a mating push-and-twist seat would be inserted directly into receptacle 14 to provide mechanical filtration capabilities, such as HEPA-type or charcoal filters. All the aforementioned components are known in the art and readily available. As an example, AVON Rubber's Protection Division produces a variety of suitable full and half-masks for purchase by law enforcement, first-responder, counter-terrorist, and military teams, as well as a variety of canister filtration units.

In accordance with the present invention, a UV-illumination tube 50 is interposed between the inhalation aperture 12 and filter assembly 40. The UV illumination tube 50 is a short multi-part cylinder, approximately 2-5", with mating push-and-twist receptacle/seats at each end for seating the filter assembly 40 and insertion into receptacle 14 of mask 10. The UV illumination tube 50 further comprises a cylindrical aluminum outer shell, and a cylindrical plastic insert (described below) that seats a plurality of elongate axially-aligned circuit boards each carrying a plurality of surface-mounted LED UV lights disposed inwardly toward the centerline of the tube 50. The UV illumination tube 50 is centrally unobstructed and incoming air from filter assembly 40 remains free to pass into the inhalation aperture 12 of the mask 10. While passing through the tube's length, the air is illuminated with high-intensity shortwave ultraviolet light from the LEDs and is thereby fully filtered and irradiated for combined chemical and biological protection. Power for the LEDs is derived from an on-board battery which may be built into the UV illumination tube 50 or the mask 10 (requiring slide-connectors along the lip of the tube 50), and/or from a solar cell (to be described) likewise mounted on the UV illumination tube 50 or the mask 10. Preferably, an on/off detent switch 52 for the LEDs is provided on the tube 50 as well.

Figure 2:
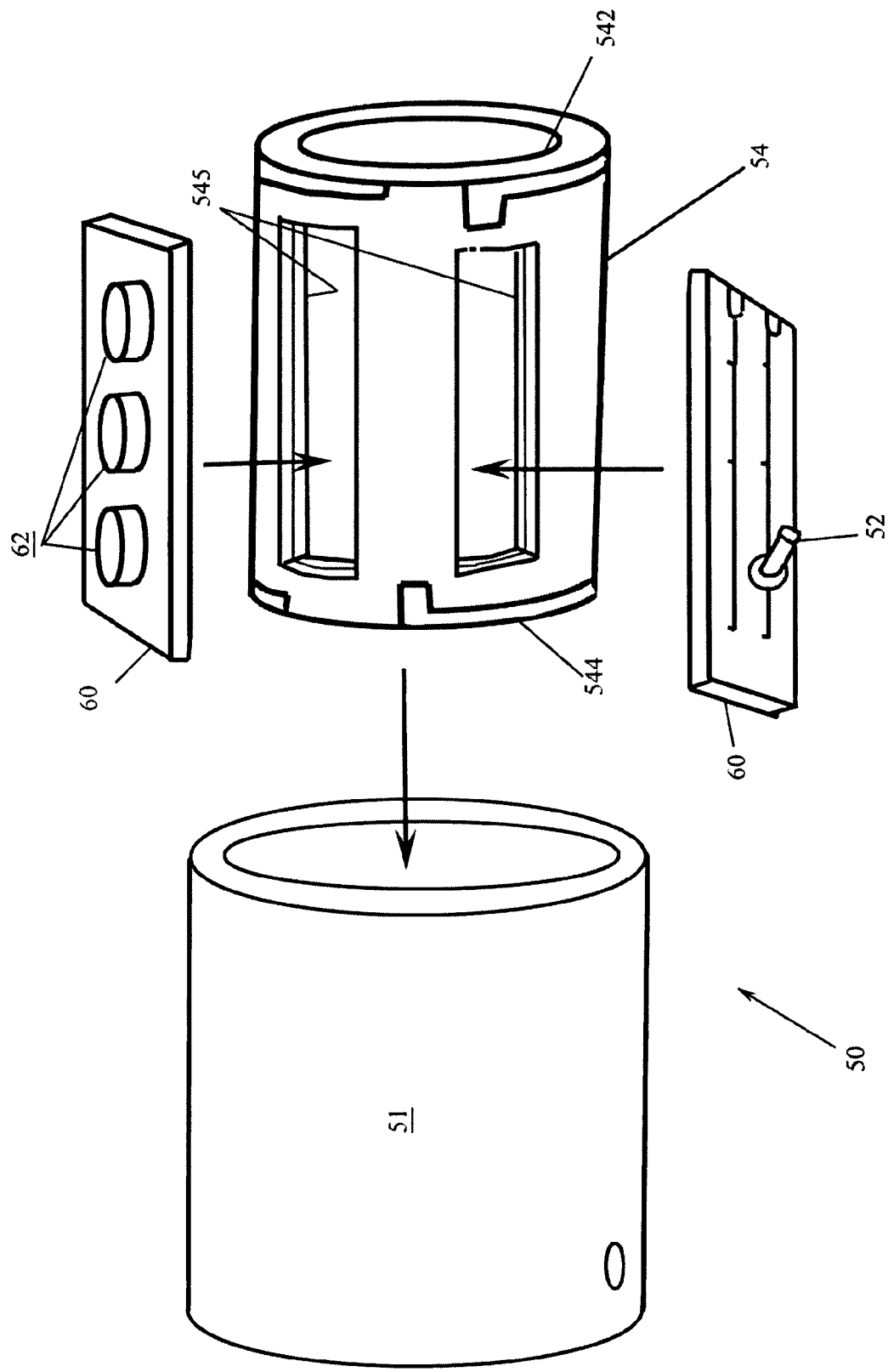
FIG. 2 is an exploded diagram of the UV illumination tube 50 as in FIG. 1.

FIG. 2 is an exploded diagram of an embodiment of the UV illumination tube 50 as in FIG. 1. In the illustrated embodiment, the UV illumination tube 50 further comprises a cylindrical aluminum outer shell 51, and a substantially cylindrical plastic insert 54 that fits conformingly within the outer shell 51. For manufacturing convenience, the plastic insert 54 is slightly longer than the aluminum outer shell 51 and protrudes at both ends, and this way mating push-and-twist receptacle 544 and push-and-twist seat 542 may be integrally molded at the opposing ends of the insert 54. One skilled in the art should understand that push-and-twist receptacle 544 and seat 542 may be replaced by screw threads, bayonet-type, or any other anchoring fixtures as a matter of design choice.

The plastic insert 54 is further formed with a plurality (here four) pass-through windows 545, though one or more may suffice. The pass-through windows 545 are elongated rectangular apertures equally-spaced and axially-aligned about the center axis of the insert 54, which centrally open into the hollow of insert 54. Each pass-through window 545 is formed with a peripheral lip to seat a corresponding circuit board 60.

The circuit board(s) 60 are likewise elongated rectangular printed circuit boards each carrying a plurality of solder-mount UV-emitting LEDs 62 protruding from one side. The UV LEDS 62 are generally low-power LEDs that shine with deep UV light for fluorescence sterilization. It has been found that the strongest disinfection occurs over the wavelengths of 240 nm~280 nm, and so a sealed 500 uW UV LED emitting within that range is suitable. For example, Sensor Electronic Technology, Inc. supplies a line of suitable UVTOP® Deep ultraviolet Light Emitting Diodes containing an AlGaN/GaN LED chip in a sealed TO39 double-lead package. Optical power out is ~500 uW. Forward current is 30 mA with a pulsed current to 200 mA at 1% duty cycle. Forward voltage is 5.5V, and reverse voltage is 6V. Peak wavelength is 250 nm, peak width is 12 nm (full width half max). The UV LEDs 62 are equally-spaced along the circuit board(s) 60 with windows directed inward toward the center axis of the insert 54. The backside of the circuit board(s) 60 contains serial printed circuit connections to the LED leads. In addition, one circuit board 60 contains the mounted detent switch 52 for selectively breaking the LED circuit, and one circuit board 60 contains a voltage regulator connected to a current chopper circuit for providing a pulsed current of 200 mA at 1% duty cycle at a forward voltage of 5.5V to the series-connected LEDs. A variety or power supply options are possible, including minimally a lithium ion battery mounted on one of the circuit boards 60 proximate the voltage regulator. One skilled in the art should understand that the battery may be mounted elsewhere, including in the mask 10 itself, in which case appropriate wiring and connection terminals are provided to the circuit board 60.

In another embodiment, a solar recharging cell (described below) is provided to prevent frequent battery replacement. The solar cell can be mounted anywhere on the surface of the tube 50 or mask 10, and is preferably mounted on an accessory visor attached to the mask for optimal sunlight exposure.

Figure 3:
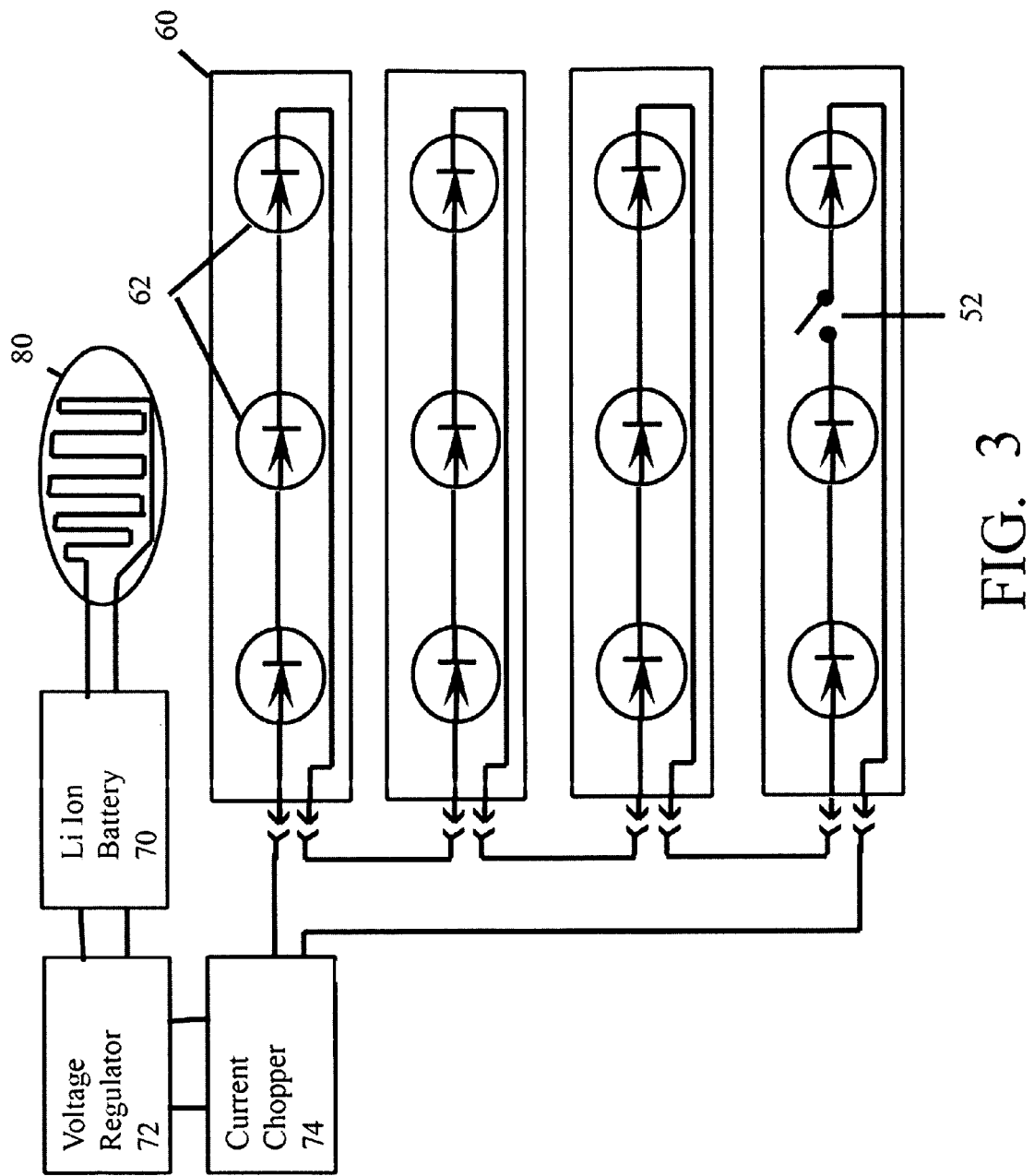
FIG. 3 is a schematic diagram of an exemplary circuit arrangement.

FIG. 3 is a schematic diagram of an exemplary circuit arrangement. Here twelve UV LEDs 62 are evenly divided among four circuit boards 60 and are connected in series by printed circuit connections. One circuit board 60 contains the mounted detent switch 52 for selectively breaking the LED circuit. The series-connected LEDs are connected to a current chopper circuit 74 that outputs pulsed current of 200 mA at 1% duty cycle at a forward voltage of 5.5V to the series-connected LEDs. The current chopper circuit 74 is connected to a voltage regulator 72 for regulating the 5.5V input power, and voltage regulator is connected to a lithium ion (or other suitable) battery 70. The battery 70 is in turn optionally connected to a solar recharging circuit 80 mounted in an exposed position on the aluminum tube 51 or elsewhere on the mask 10. A variety or power supply options are possible, including minimally a lithium ion battery mounted on one of the circuit boards 60 proximate the voltage regulator.

Figure 4:
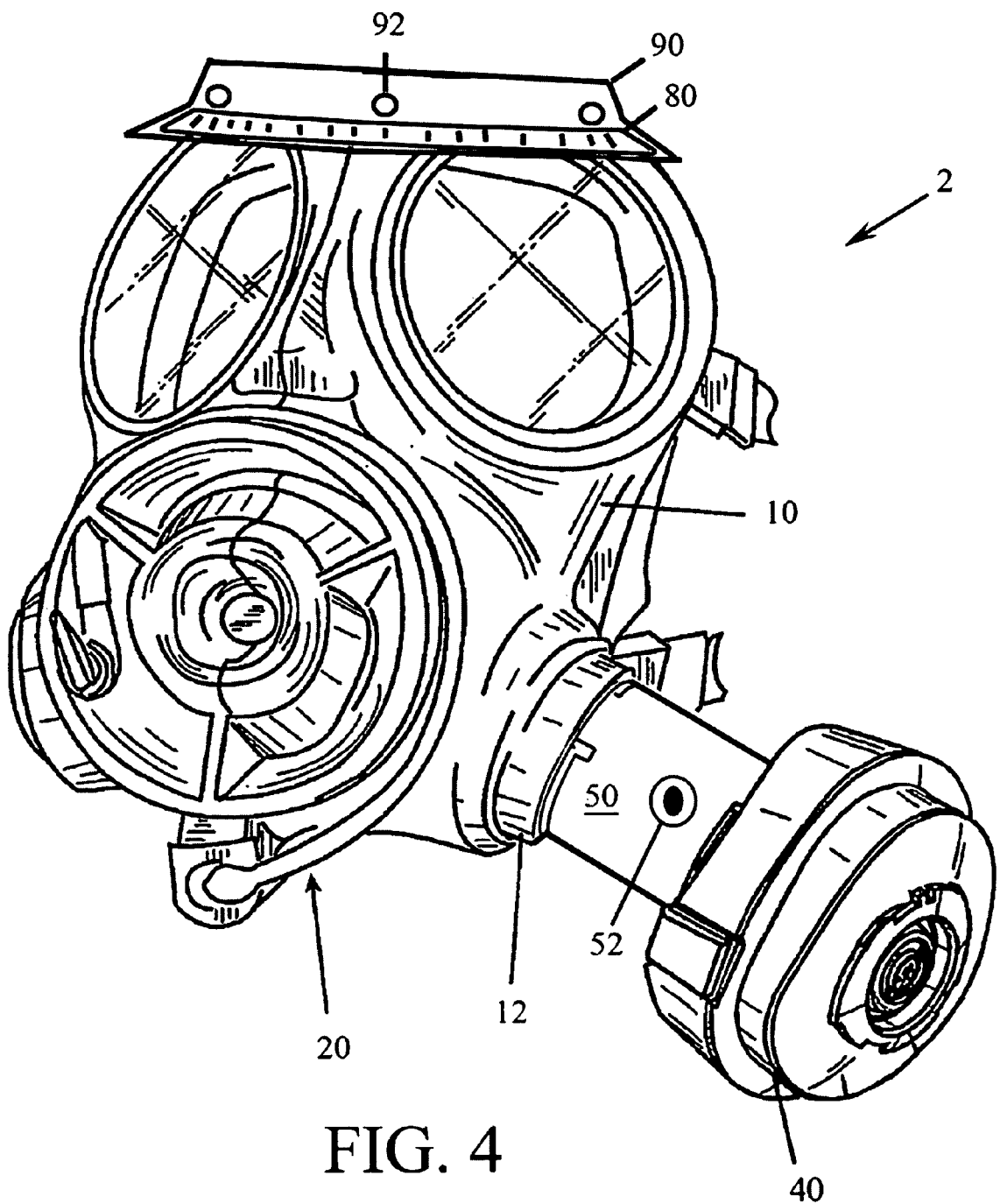
FIG. 4 is a perspective view of an accessory visor 90 for conveniently mounting the solar cell 80 for optimal sun exposure.

FIG. 4 is a perspective view of an accessory visor 90 for conveniently mounting the solar cell 80 for optimal sun exposure. Visor 90 is attached by snaps 92 or other fasteners above the brow of the mask 10 to serve as a sun shield. The visor 90 includes a brim upon which the solar cell 80 may be adhered lengthwise for optimal exposure to the sun and optimal recharging capability. The wiring to the solar cell 80 may be conveniently run through the peripheral rubber flanges of the mask 10 to the UV illumination tube 50 where they remain hidden. One skilled in the art will readily understand that the solar cell 80 may be relied upon to fully power the LEDs 62, in which case the battery 70 can be eliminated, though primary or at least backup battery power is preferred.

It should now be apparent that the above-described invention provides a novel combination chemical and biological protection mask in a compact portable self-contained form factor to which conventional gas mask users are well-accustomed, and the a miniaturized low-power UV LED-light array incorporated therein adds a completely new level of biological protection to the capabilities of an otherwise conventional filter mask.

Indeed, it should be understood that various changes may be made in the form, details, arrangement and proportions of the parts. Such changes do not depart from the scope of the invention which comprises the matter shown and described herein and set forth in the appended claims.

I claim:

1. A gas mask for operation in contaminated areas, comprising:
   a mask portion for covering at least the nose and mouth of a user;
   a one way exhalation valve mounted on said mask portion;
   a coupling to an inhalation opening through said mask portion;
   a UV-illumination tube attachable at one end to said coupling, said UV illumination tube comprising a central air passage, a first plurality of UV LED lights axially aligned along a periphery of said central air passage, and a second plurality of UV LED lights axially aligned along a periphery of said central air passage and radially offset from said first plurality of UV LED lights;
   a filter assembly attachable to another end of said UV illumination tube.

2. The gas mask according to claim 1, wherein all of said first plurality of UV LED lights and second plurality of UV LED lights emit light within a range of from 240 nm to about 280 nm wavelength.

3. The gas mask according to claim 1, wherein said first plurality of UV LED lights are commonly mounted on a first circuit board, and said second plurality of UV LED lights are commonly mounted on a second circuit board.

4. The gas mask according to claim 1, further comprising a battery connected to a voltage regulator, and a current chopping circuit connected between said voltage regulator and said first plurality of UV LED lights and second plurality of UV LED lights for providing pulsed current to said lights.

5. The gas mask according to claim 1, further comprising a solar cell for powering said first plurality of UV LED lights and second plurality of UV LED lights.

6. The gas mask according to claim 4, further comprising a solar cell for recharging said battery.

7. The gas mask according to claim 5, wherein said solar cell is mounted atop a visor attached to said mask.

8. The gas mask according to claim 6, wherein said solar cell is mounted atop a visor attached to said mask.

9. A gas mask for operation in contaminated areas, comprising:
   a mask portion for covering at least the nose and mouth of a user;
   a one way exhalation valve mounted on said mask portion;
   a coupling to an inhalation opening through said mask portion;
   a UV-illumination tube attachable at one end to said coupling, said UV illumination tube further comprising an aluminum tube, a plastic insert positioned inside said aluminum tube, a first circuit board seated within said insert, a second circuit board seated within said insert angularly offset from said first circuit board, a first plurality of UV LED lights axially mounted along said first circuit board, and a second plurality of UV LED lights axially mounted along said second circuit board; and
   a filter assembly attachable to another end of said UV illumination tube.

10. The gas mask according to claim 9, wherein all of said first plurality of UV LED lights and second plurality of UV LED lights emit light within a range of from 240 nm to about 280 nm wavelength.

11. The gas mask according to claim 9, wherein said first plurality of UV LED lights are uniformly spaced in a line along said first circuit board.

12. The gas mask according to claim 9, further comprising a battery connected to a voltage regulator, and a current chopping circuit connected between said voltage regulator and said first plurality of UV LED lights and second plurality of UV LED lights for providing pulsed current thereto.

13. The gas mask according to claim 9, further comprising a solar cell for powering said first plurality of UV LED lights and second plurality of UV LED lights.

14. The gas mask according to claim 12, further comprising a solar cell for recharging said battery.

15. The gas mask according to claim 13, wherein said solar cell is mounted atop a visor attached to said mask.

16. The gas mask according to claim 14, wherein said solar cell is mounted atop a visor attached to said mask.

17. An attachment to a gas mask and filter combination for operation in contaminated areas, comprising a UV-illumination tube attachable at one end to said gas mask and at another end to a filter, said UV illumination tube comprising a tubular outer shell, a cylindrical plastic insert positioned concentrically inside said outer shell, said cylindrical insert defined by a plurality of windows, a plurality of circuit boards seated within the plurality of windows in said plastic insert, and a plurality of UV LED lights axially mounted on said circuit boards.

18. The attachment according to claim 17, wherein said plurality of UV LED lights emit light within a range of from 240 nm about 280 nm wavelength.

19. The attachment according to claim 17, wherein said plurality of UV LED lights are uniformly distributed in groups on said plurality of circuit boards.

20. The attachment according to claim 17, further comprising a battery connected to a voltage regulator, and a current chopping circuit connected between said voltage regulator and said UV LED lights for providing pulsed current thereto.

21. The attachment according to claim 17, further comprising a solar cell for powering said UV LED lights and/or recharging a battery.

* * * * *